(12) United States Patent
Nishigishi

(10) Patent No.: US 9,937,069 B2
(45) Date of Patent: Apr. 10, 2018

(54) PUSHER GUIDE WIRE AND DELIVERY SYSTEM COMPRISING THE SAME

(71) Applicant: ASAHI INTECC CO., LTD., Nagoya-shi, Aichi (JP)

(72) Inventor: Makoto Nishigishi, Owariasahi (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 161 days.

(21) Appl. No.: 14/944,912

(22) Filed: Nov. 18, 2015

(65) Prior Publication Data
US 2016/0302949 A1    Oct. 20, 2016

(30) Foreign Application Priority Data

Apr. 15, 2015    (JP) ................. 2015-083682

(51) Int. Cl.
*A61F 2/966* (2013.01)
*A61F 2/82* (2013.01)
(Continued)

(52) U.S. Cl.
CPC .............. *A61F 2/966* (2013.01); *A61F 2/82* (2013.01); *A61M 25/09* (2013.01);
(Continued)

(58) Field of Classification Search
CPC .............. A61F 2/966; A61F 2002/9534; A61F 2002/9505; A61F 2002/9522; A61F 2002/9665; A61F 2250/0098; A61M 25/09
See application file for complete search history.

(56) References Cited

U.S. PATENT DOCUMENTS 6,833,003 B2    12/2004    Jones et al.
6,960,227 B2    11/2005    Jones et al.
(Continued)

FOREIGN PATENT DOCUMENTS

EP    1 374 801 B1    4/2006
EP    2 777 650 A1    9/2014
JP    4574131 B2    11/2010

OTHER PUBLICATIONS

Mar. 9, 2017 Office Action issued in European Patent Application No. 15 197 421.9.
(Continued)

*Primary Examiner* — Katherine Rodjom
(74) *Attorney, Agent, or Firm* — Oliff PLC

(57) ABSTRACT

A pusher guide wire and a delivery system can smoothly pass through the inside of even a curved blood vessel without causing excessive burden to a stent, a catheter, and the like. A pusher guide wire has a tubular member capable of moving in a radial direction relative to a core shaft of the pusher guide wire. When the pusher guide wire is used together with a stent in a delivery system, the tubular member makes contact with the stent in an appropriate manner when passing through the inside of a curved blood vessel. The stent may include a proximal end engagement portion provided at a proximal end of the stent. When the stent is placed so that the proximal end engagement portion engages with the pusher guide wire, the stent can be pulled back inside the catheter by pulling the pusher guide wire in the proximal direction.

9 Claims, 9 Drawing Sheets

(51) Int. Cl.
*A61M 25/09* (2006.01)
*A61F 2/95* (2013.01)
(52) U.S. Cl.
CPC ............... *A61F 2002/9534* (2013.01); *A61F 2230/0067* (2013.01); *A61F 2250/0098* (2013.01)

(56) References Cited

U.S. PATENT DOCUMENTS

| | | |
|---|---|---|
| 7,201,769 B2 | 4/2007 | Jones et al. |
| 2006/0229697 A1 | 10/2006 | Gerdts et al. |
| 2007/0198076 A1* | 8/2007 | Hebert .................. A61F 2/962 623/1.11 |
| 2010/0094394 A1 | 4/2010 | Beach et al. |
| 2014/0277357 A1* | 9/2014 | Slazas .................. A61F 2/966 623/1.12 |

OTHER PUBLICATIONS

Aug. 19, 2016 Extended European Search Report issued in European Patent Application No. 15 197 421.9.

* cited by examiner

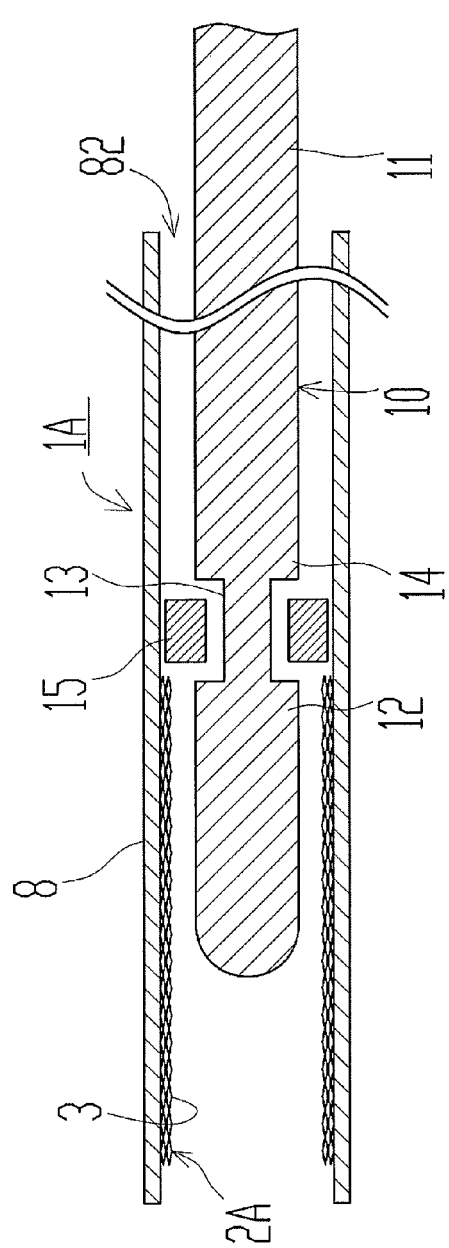
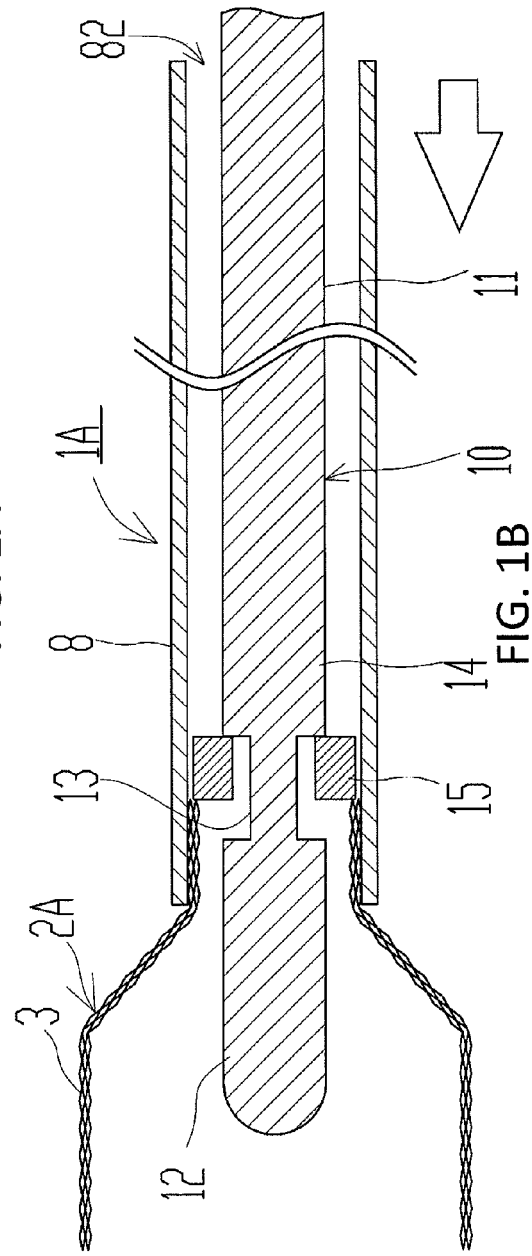
FIG. 1A
FIG. 1B

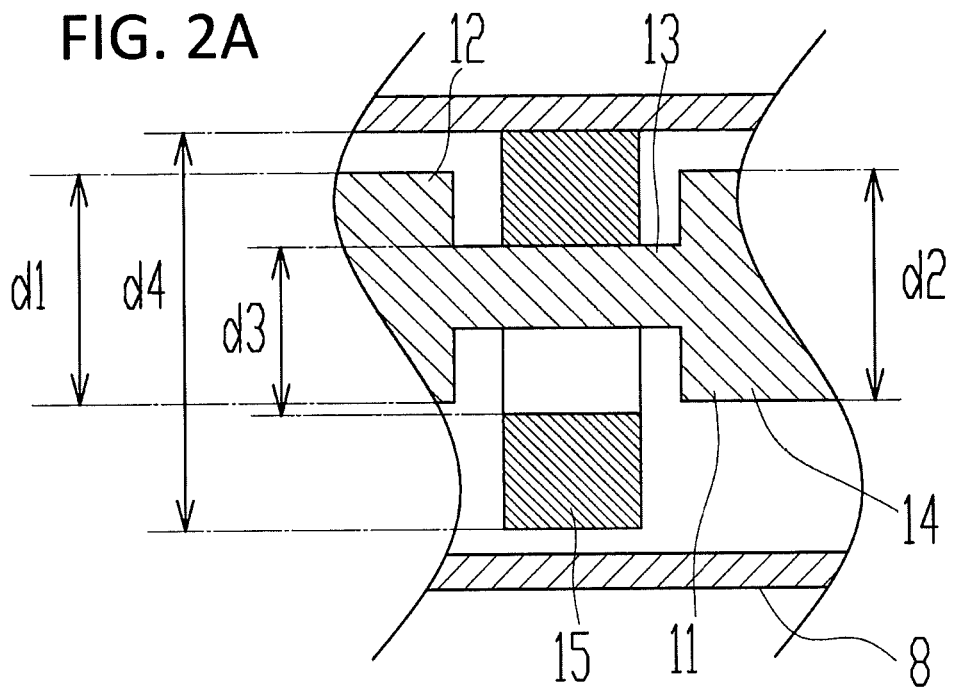
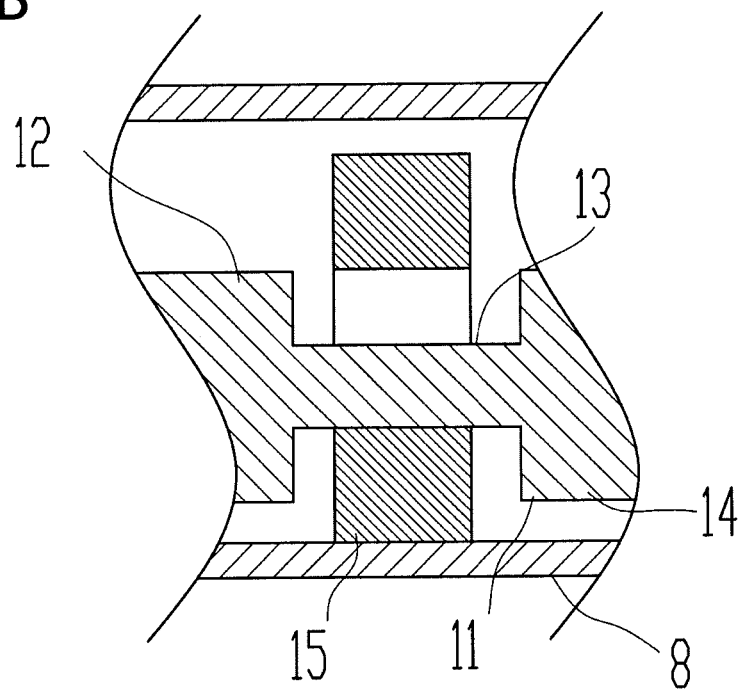

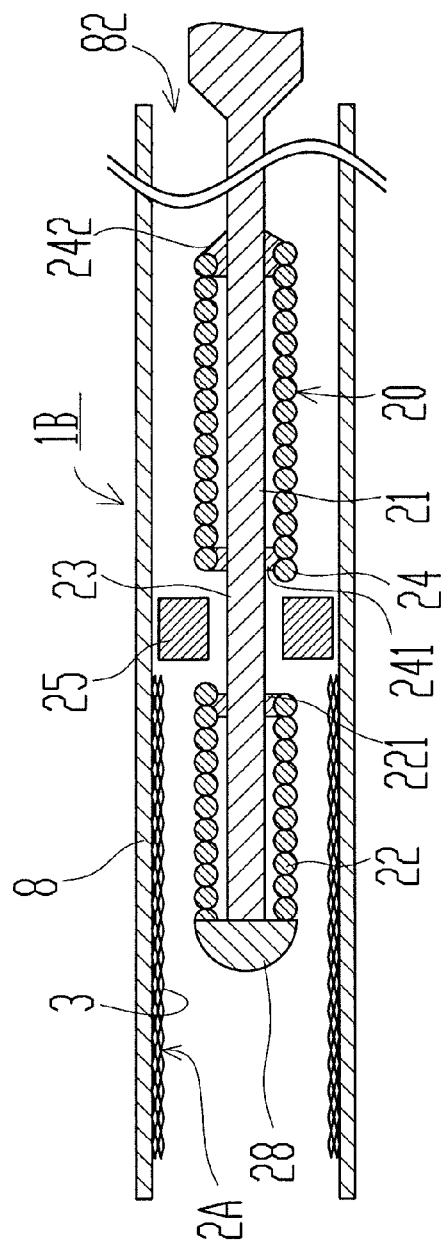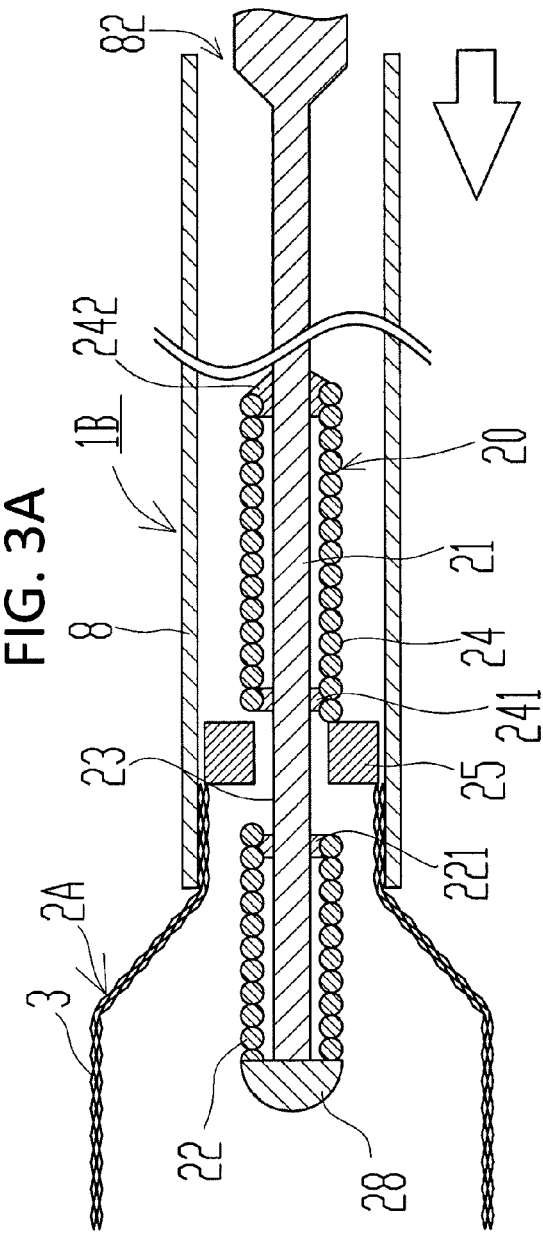
FIG. 3A
FIG. 3B

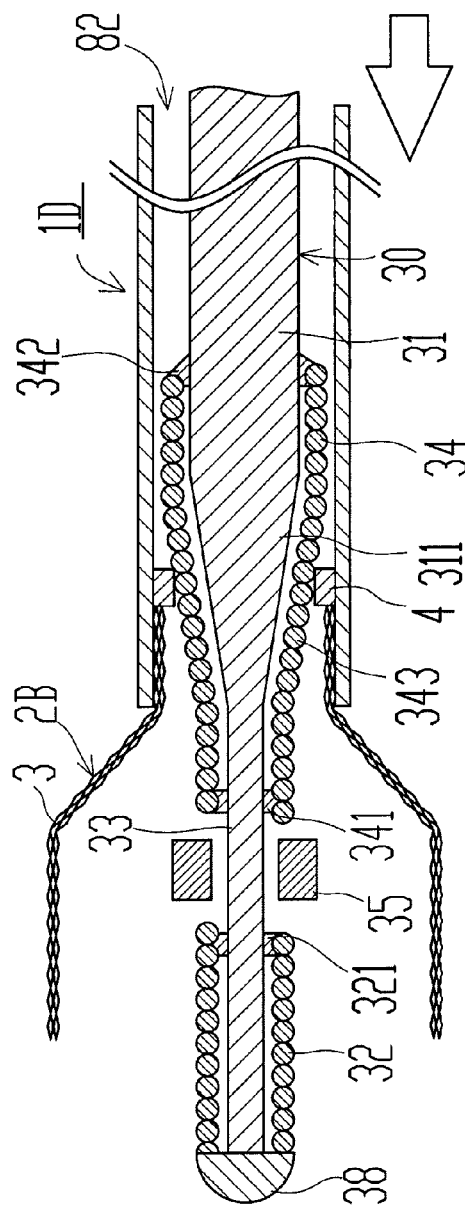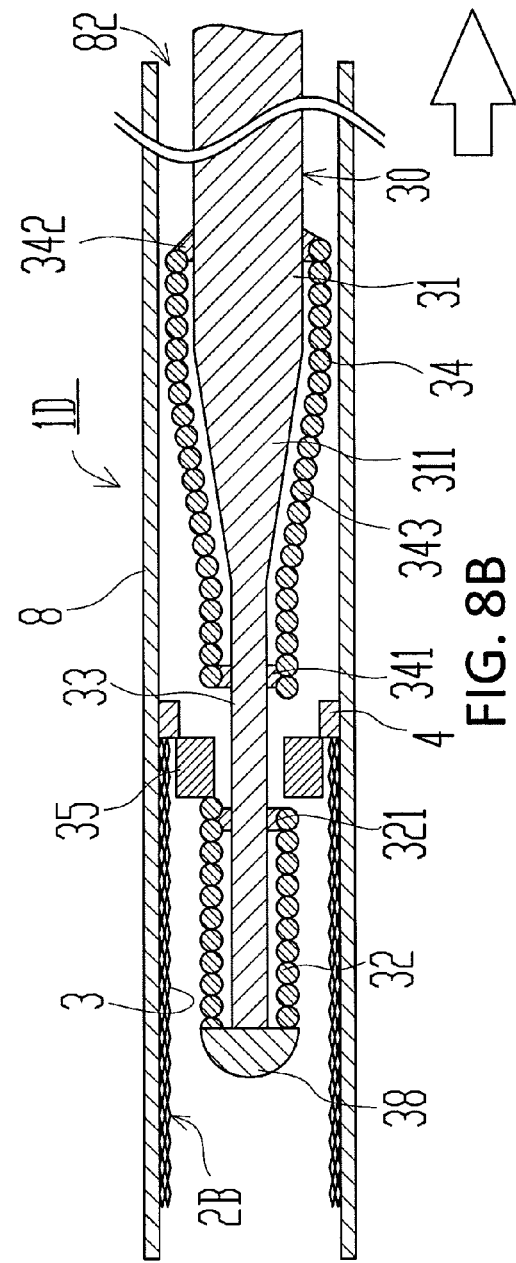

PUSHER GUIDE WIRE AND DELIVERY SYSTEM COMPRISING THE SAME

CROSS REFERENCE TO RELATED APPLICATION

This application claims priority to Japanese Application No. 2015-083682 filed on Apr. 15, 2015, the content of which is incorporated by reference herein in its entirety.

BACKGROUND

The disclosed embodiments relate to a medical device. Specifically, the disclosed embodiments relate to a pusher guide wire for delivering a stent stored in a catheter to a target site, and a delivery system comprising the pusher guide wire.

A conventional method for delivering (carrying or conveying) a stent to a target site involves storing the stent in a distal end portion of a catheter in a state in which a pusher guide wire is disposed within a lumen of the stent, advancing the catheter to the target site, and then pushing the pusher guide wire in the distal direction to release the stent to the target site through the distal end of the catheter.

For example, Japanese Patent No. 4574131 discloses a system for delivering an expandable stent. The stent includes a core shaft; a proximal columnar member covering a proximal portion of the core shaft and fixed to the core shaft; a middle columnar member covering a central portion of the core shaft at a position distal to the proximal columnar member; and a distal columnar member covering a distal portion of the core shaft and fixed to the core shaft at a position distal to the middle columnar member.

However, in the delivery system disclosed in Japanese Patent No. 4574131, when the pusher guide wire and the stent pass through the inside of a curved blood vessel, the curved pusher guide wire may disadvantageously press against the stent and the catheter, preventing the advancement and rotation of the pusher guide wire or causing the stent to bend.

SUMMARY

An objective of the disclosed embodiments is to provide a pusher guide wire that allows a stent, a catheter, and the like to smoothly pass through a curved blood vessel. Another objective of the disclosed embodiments is to provide a delivery system capable of delivering a stent to an appropriate location.

The disclosed embodiments include a pusher guide wire for delivering a stent to a target site. The pusher guide wire includes a core shaft and a tubular member. The core shaft includes a first large-diameter portion; a small-diameter portion positioned proximal to the first large-diameter portion and having an outer diameter smaller than that of the first large-diameter portion; and a second large-diameter portion positioned proximal to the small-diameter portion and having an outer diameter larger than that of the small-diameter portion. The tubular member is located between a proximal end of the first large-diameter portion and a distal end of the second large-diameter portion such that the small-diameter portion of the core shaft extends through an inside of the tubular member. The tubular member is not fixed to the core shaft and is capable of moving in a radial direction relative to the core shaft.

Because the tubular member is not fixed to the core shaft in the aforementioned configuration, the tubular member can move in a radial direction in an appropriate manner depending on the curvature of the catheter and can be brought into contact with the stent when the pusher guide wire is inserted into a curved catheter. As a result, a stent can be delivered smoothly to a target site because a clearance between the catheter and the pusher guide wire can be secured. Further, the core shaft can be smoothly, easily, and independently rotated because the core shaft is spaced apart from the catheter (the stent) by the tubular member. Moreover, the catheter does not rotate when the core shaft rotates, reducing a risk of damaging the inner wall of a blood vessel and the like.

The disclosed embodiments also include a pusher guide wire comprising a core shaft; a first coil body covering the core shaft and fixed to the core shaft; a second coil body covering the core shaft and fixed to the core shaft at a position proximal to the first coil body, the first coil body and the second coil body being spaced apart from each other in an axial direction of the pusher guide wire; and a tubular member disposed between the first coil body and the second coil body such that the core shaft extends through an inside of the tubular member. The tubular member is not fixed to the core shaft and is capable of moving in a radial direction relative to the core shaft.

Because the tubular member is not fixed to the core shaft in the aforementioned configuration, the tubular member can move in a radial direction in an appropriate manner depending on the curvature of the catheter and can be brought into contact with the stent when the pusher guide wire is inserted into a curved catheter. As a result, a stent can be delivered smoothly to a target site because a clearance between the catheter and the pusher guide wire can be secured. Further, the core shaft can be independently rotated because the core shaft is spaced apart from the catheter (the stent) by the tubular member. Moreover, the catheter does not rotate when the core shaft rotates, reducing a risk of damaging the inner wall of a blood vessel.

The second coil body preferably has a tapered portion having an outer diameter that increases toward a proximal end of the pusher guide wire. In this configuration, a force for directing the stent in the distal direction can be exerted by bringing the tapered portion of the second coil body into contact with the stent and pressing the tapered portion of the second coil body against the stent. As described above, the stent can be delivered more smoothly to a target site without impairing the flexibility of the pusher guide wire because a separate member does not need to be provided as a means for pressing the stent.

The tubular member is preferably formed of a radiopaque material. In this configuration, an operator can detect the position of the stent by detecting the position of the tubular member. Therefore, it is not necessary to attach a radiopaque marker member to the stent.

The disclosed embodiments also include a delivery system comprising a pusher guide wire and a stent to be delivered with the pusher guide wire. As described above, the pusher guide wire includes a second coil body having a tapered portion with an outer diameter that increases toward the proximal end of the pusher guide wire. A proximal end portion of the stent has a proximal end engagement portion that protrudes toward an outer periphery of the core shaft and is located between the tapered portion and the tubular member in an axial direction of the core shaft. An inner diameter of the stent at the proximal end engagement portion is smaller than an outer diameter of the second coil body at the tapered portion.

In the aforementioned configuration, the proximal end engagement portion is provided at the proximal end portion of the stent, and therefore the tapered portion of the second coil body can be easily brought into contact with the stent. Consequently, a force for directing the stent in the distal direction can easily be exerted. Further, the stent can be retracted into the catheter after having been partially released from the catheter by pulling the pusher guide wire back in the proximal direction, thereby bringing the tubular member into contact with the proximal end engagement portion of the stent.

The disclosed embodiments also include a delivery system comprising a pusher guide wire comprising the first coil body and the second coil body, and a stent to be delivered with the pusher guide wire. The distal end portion of the stent has a distal end engagement portion protruding toward the core shaft, and an inner diameter of the stent at the distal engagement portion is smaller than an outer diameter of the distal end of the tubular member.

In the aforementioned configuration, a force for directing the stent in the distal direction can be exerted by bringing the tubular member into contact with the distal end engagement portion of the stent and pressing the tubular member against the distal end engagement portion of the stent. The stent can be delivered more smoothly to a target site without impairing the flexibility of the pusher guide wire because a separate member does not need to be provided as a means for pressing the stent described above. In particular, delivery is easier because a risk of bending the stent inside of the catheter is reduced as compared with a case where the stent is pushed from its proximal end portion.

The pusher guide wire according to the disclosed embodiments has an advantageous effect in that a stent, a catheter, and the like can smoothly pass through the inside of a curved blood vessel. Further, the delivery system according to the disclosed embodiments has an advantageous effect in that a stent can be smoothly delivered to an appropriate location.

BRIEF DESCRIPTION OF THE DRAWINGS

FIGS. 1A and 1B each show a cross-sectional view of a delivery system according to the disclosed embodiments.

FIGS. 2A and 2B each show a partial enlarged cross-sectional view of the delivery system shown in FIGS. 1A and 1B.

FIGS. 3A and 3B each show a cross-sectional view of a delivery system according to the disclosed embodiments.

FIGS. 8A and 8B each show a cross-sectional view of the delivery system shown in FIG. 7 in operation.

DETAILED DESCRIPTION OF EMBODIMENTS

Figure 4A:
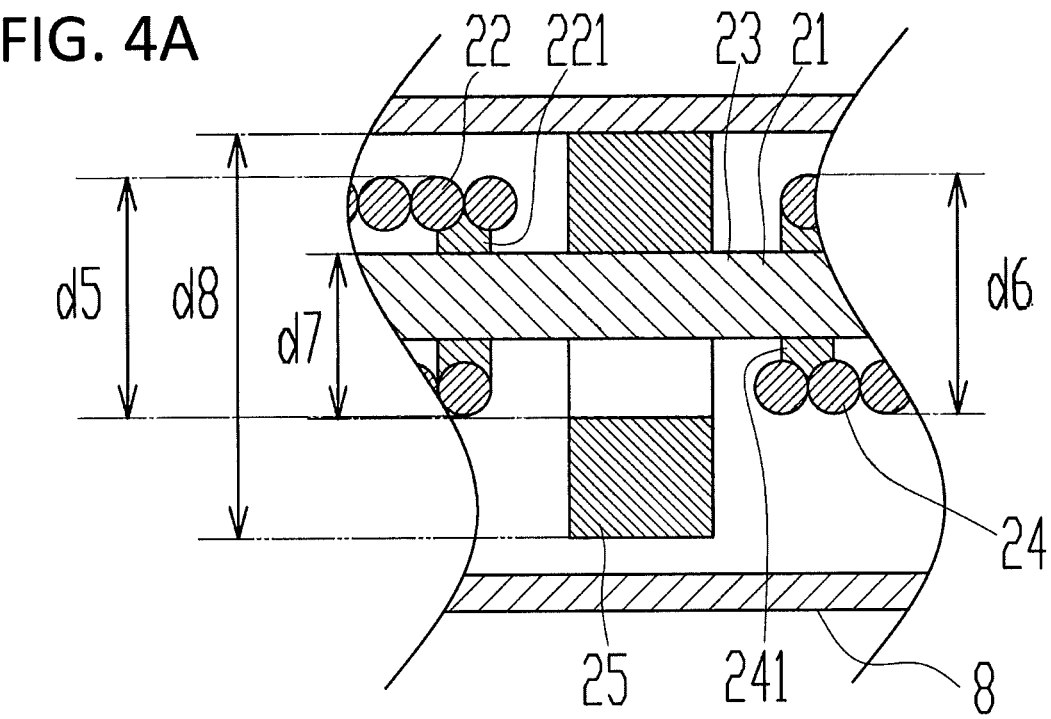
FIGS. 4A and 4B each show a partial enlarged cross-sectional view of the delivery system shown in FIGS. 3A and 3B.

Examples of the pusher guide wire and the delivery system according to the disclosed embodiments will be described in detail below. However, the disclosed embodiments are not limited to the examples described below, and modifications in design can be made in an appropriate manner. Further, note that the left side in FIGS. 1A to 9 corresponds to the distal end (the front end) which is to be inserted into the body, and the right side corresponds to the proximal end (the back end) which is to be operated by an operator such as a physician. For parts in common with each configuration, description will be omitted and the same reference numbers will be assigned in the figures.

As shown in FIG. 1A, a delivery system 1A to be inserted into a catheter 8 comprises a self-expandable stent 2A and a pusher guide wire 10.

The catheter 8 is a tube-like body into which the pusher guide wire 10 can be inserted, and the stent 2A and the pusher guide wire 10 are inserted through a proximal end opening 82 of the catheter 8.

The stent 2A comprises a body portion 3 having a mesh-like cylindrical shape. Note that there is no particular limitation for a material of the stent 2A, and any known material can be used.

The pusher guide wire 10 comprises a core shaft 11 having a hemispherical distal end. Further, the core shaft 11 comprises a first large-diameter portion 12 having an outer diameter smaller than an inner diameter of the stent 2A; a small-diameter portion 13 positioned proximal to the first large-diameter portion 12 and having an outer diameter smaller than that of the first large-diameter portion 12; and a second large-diameter portion 14 positioned proximal to the small-diameter portion 13 and having an outer diameter larger than that of the small-diameter portion 13. Note that the core shaft 11 is preferably formed of a stainless steel (for example, SUS304, SUS316, and the like) or a superelastic alloy such as an Ni—Ti alloy.

Further, a tubular member 15 is disposed at the small-diameter portion 13 of the pusher guide wire 10 such that the small-diameter portion 13 of the core shaft 11 extends through an inside of the tubular member 15. That is, the tubular member 15 is located between a proximal end of the first large-diameter portion 12 and a distal end of the second large-diameter portion 14.

Further, the tubular member 15 is not fixed to the core shaft 11, and the dimension and shape of the tubular member 15 is configured so that it is capable of moving in a radial direction relative to the core shaft 11, as shown in FIGS. 2A and 2B. Specifically, an inner diameter d3 of the tubular member 15 is smaller than each of an outer diameter d1 of the first large-diameter portion 12 and an outer diameter d2 of the second large-diameter portion 14 (d1>d3, d2>d3). Further, an outer diameter d4 of the tubular member 15 is larger than each of the outer diameter d1 of the first large-diameter portion 12 and the outer diameter d2 of the second large-diameter portion 14 (d4>d1, d4>d2).

Note that the tubular member 15 is preferably formed of a radiopaque material such as gold, platinum, tungsten, or an alloy comprising these elements. Thereby, an operator can detect the position of the stent 2A by detecting the position of the tubular member 15 without needing to add a radiopaque marker and the like to the stent 2A.

The tubular member 15 is not fixed to the core shaft 11 in the configuration described above, and thus an outer periphery of the tubular member 15 can make contact with an inner periphery of the catheter 8 in an appropriate manner as shown in FIGS. 2A and 2B when the stent 2A and the pusher guide wire 10 pass through the inside of a curved blood vessel. Further, even in a case where the core shaft 11 is rotated, the tubular member 15 and the catheter 8 will not rotate. Therefore, a risk of damaging the inner wall of a blood vessel when rotating the core shaft 11 can be reduced.

Further, the stent 2A can be delivered smoothly to a target site because a clearance between the core shaft 11 and the catheter 8 can be secured by the presence of the tubular member 15.

Moreover, the core shaft 11 can rotate independently of the tubular member 15 and the catheter 8 as described above, leading to excellent operability.

Further, the outer diameter d4 of the tubular member 15 is designed to be larger than an inner diameter of the stent 2A when the stent 2A is stored inside the catheter 8. Thus, the stent 2A can be pushed out of the catheter 8 by the tubular member 15 in the distal direction as shown in FIG. 1B.

Meanwhile, examples of methods of coupling the tubular member 15 to the core shaft 11 include a method in which a plate-like material made of a metal or a resin is loosely wound around the small-diameter portion 13, and then both end portions of the plate-like material are joined together to form the tubular member 15. Examples further include a method in which the tubular member 15 is formed with a heat-shrinkable tube, and then heat is applied at a location of the small-diameter portion 13 to produce the tubular member 15 sandwiched between the first large-diameter portion 12 and the second large-diameter portion 14.

Below, the operating procedure of the delivery system 1A will be described.

After advancing the catheter 8 to a target site, an operator pushes the core shaft 11 of the pusher guide wire 10 in the distal direction with the intention of releasing the stent 2A stored in the catheter 8 to the target site. Then, a proximal end of the tubular member 15 makes contact with the distal end of the second large-diameter portion 14, and at the same time, a distal end of the tubular member 15 makes contact with a proximal end of the stent 2A. Then, the stent 2A is pushed out of the catheter 8 by further pushing the core shaft 11, and the stent 2A undergoes self-expansion upon release from the catheter 8 as shown in FIG. 1B. Note that the pusher guide wire 10 and the catheter 8 are retrieved from the inside of the blood vessel after the stent 2A is completely pushed out of the catheter 8.

As shown in FIG. 3A, a delivery system 1B comprises the self-expandable stent 2A and a pusher guide wire 20.

The pusher guide wire 20 comprises a first coil body 22 covering a core shaft 21 and fixed to the core shaft 21. A distal end portion of the first coil body 22 is joined to a distal end portion 28 of the core shaft 21, and a proximal end portion of the first coil body 22 is bonded to the core shaft 21 through a first joining region 221. Further, the pusher guide wire 20 comprises a second coil body 24 covering the core shaft 21 and fixed to the core shaft 21 proximal to the first coil body 22 such that the first coil body 22 and the second coil body are spaced apart from each other in an axial direction of the pusher guide wire 20. A distal end portion of the second coil body 24 is joined to the core shaft 21 through a second joining region 241, and a proximal end portion of the second coil body 24 is joined to the core shaft 21 through a third joining region 242.

The first coil body 22 and the second coil body 24 are preferably formed of a stainless steel (for example, SUS304, SUS316, and the like) or a superelastic alloy such as an Ni—Ti alloy, as in the case of the core shaft 21. Further, the joining regions 221, 241, and 242 and the distal end portion 28 of the core shaft 21 are preferably formed of a solder material (for example, an aluminum alloy solder, silver solder, gold solder, or the like), a metal solder (for example, an Au—Sn alloy and the like), or the like.

Figure 4B:
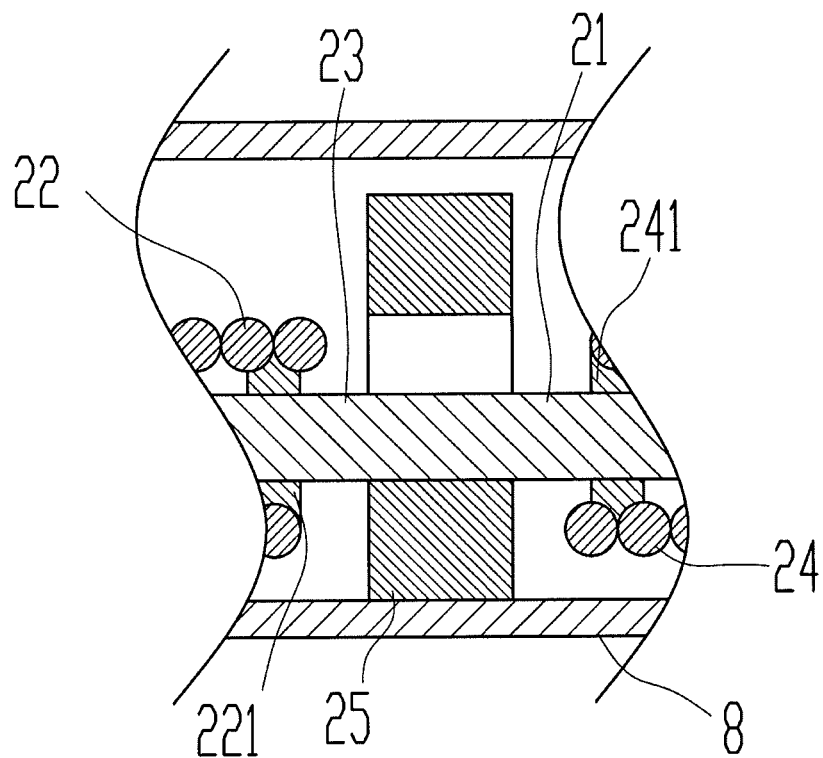

The pusher guide wire 20 further comprises a tubular member 25 that is located at a small-diameter portion 23 of the pusher guide wire 20 formed between the first coil body 22 and the second coil body 24. The small-diameter portion 23 of the pusher guide wire 20 extends through an inside of the tubular member 25. The tubular member 25 is not fixed to the core shaft 21 and is capable of moving in a radial direction relative to the core shaft 21 as shown in FIGS. 4A and 4B. Specifically, an inner diameter d7 of the tubular member 25 is smaller than each of an outer diameter d5 of the first coil body 22 and an outer diameter d6 of the second coil body 24 (d5>d7, d6>d7). Further, an outer diameter d8 of the tubular member 25 is larger than each of the outer diameter d5 of the first coil body 22 and the outer diameter d6 of the second coil body 24 (d8>d5, d8>d6).

Since the tubular member 25 is not fixed to the core shaft 21 in the configuration as described above, an outer periphery of the tubular member 25 can make contact with the inner periphery of the catheter 8 in an appropriate manner when the stent 2A and the pusher guide wire 20 pass through the inside of a curved blood vessel, as shown in FIGS. 4A and 4B. Further, even in a case where the core shaft 21 is rotated, the tubular member 25 and the catheter 8 will not rotate. Therefore, a risk of damaging the inner wall of a blood vessel when rotating the core shaft 21 can be reduced.

Further, the stent 2A can be delivered smoothly to a target site because a clearance between the core shaft 21 and the catheter 8 is secured by the presence of the tubular member 25.

Moreover, the core shaft 21 can rotate independently of the tubular member 25 and the catheter 8 as described above, leading to excellent operability.

Further, since the outer diameter d8 of the tubular member 25 is larger than the inner diameter of the stent 2A when the stent 2A is stored inside the catheter 8. Thus, the stent 2A can be pushed out of the catheter 8 by the tubular member 25 in the distal direction, as shown in FIG. 3B.

Below, the operating procedure of the delivery system 1B will be described.

After advancing the catheter 8 to a target site, an operator pushes the core shaft 21 of the pusher guide wire 20 in the distal direction with the intention of releasing the stent 2A stored in the catheter 8 to the target site. Then, a proximal end of the tubular member 25 makes contact with a distal end of the second coil body 24, and at the same time, a distal end of the tubular member 25 makes contact with the proximal end of the stent 2A.

Then, the stent 2A is pushed out of the catheter 8 by further pushing the core shaft 21, and the stent 2A undergoes self-expansion upon release from the catheter 8 as shown in FIG. 3B. Note that the pusher guide wire 20 and the catheter 8 are retrieved from the inside of the blood vessel after the stent 2A is completely pushed out of the catheter 8.

Figure 5A:
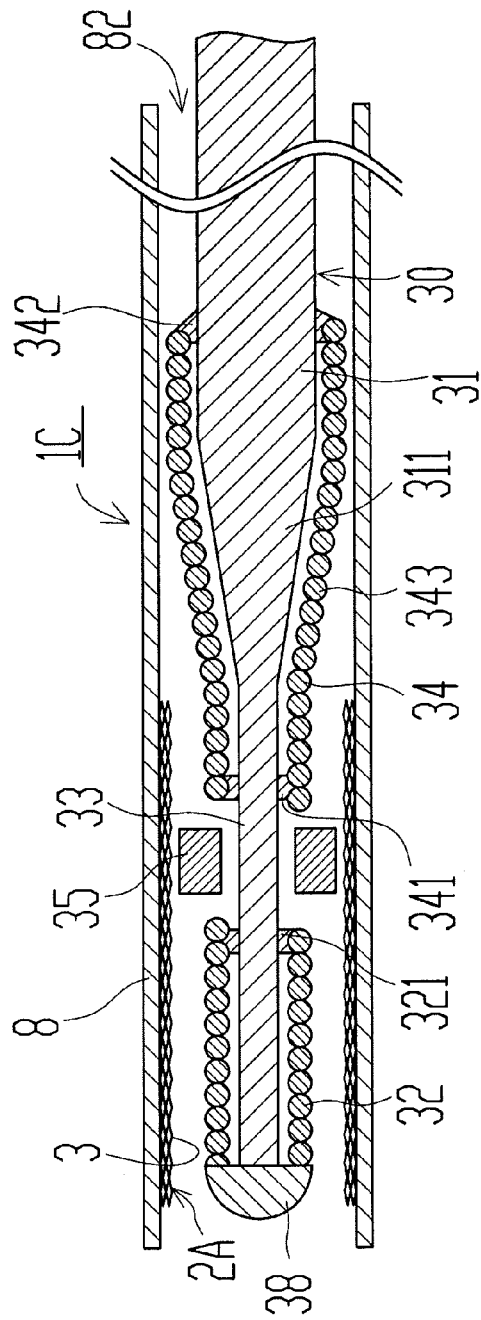
FIGS. 5A and 5B each show a cross-sectional view of a delivery system according to the disclosed embodiments.

As shown in FIG. 5A, a delivery system 1C comprises the self-expandable stent 2A and a pusher guide wire 30.

The pusher guide wire 30 comprises a first coil body 32 covering a core shaft 31 and fixed to the core shaft 31. A distal end portion of the first coil body 32 is joined to a distal end portion 38 of the core shaft 31, and a proximal end portion of the first coil body 32 is joined to the core shaft 31 through a first joining region 321. Further, the pusher guide wire 30 comprises a second coil body 34 covering the core shaft 31 and fixed to the core shaft 31 proximal to the first coil body 32 such that the first coil body 32 and the second coil body 34 are spaced apart from each other in an axial direction of the pusher guide wire 30. A distal end portion of the second coil body 34 is joined to the core shaft 31 through a second joining region 341, and a proximal end portion of the second coil body 34 is joined to the core shaft 31 through a third joining region 342. Note that the core shaft 31 has a tapered portion 311 with an outer diameter that increases toward a proximal end of the pusher guide wire 30, the tapered portion 311 being covered with the second coil body 34. The second coil body 34 also has a tapered portion 343 with an outer diameter that increases toward the proximal end of the pusher guide wire 30.

Figure 6A:
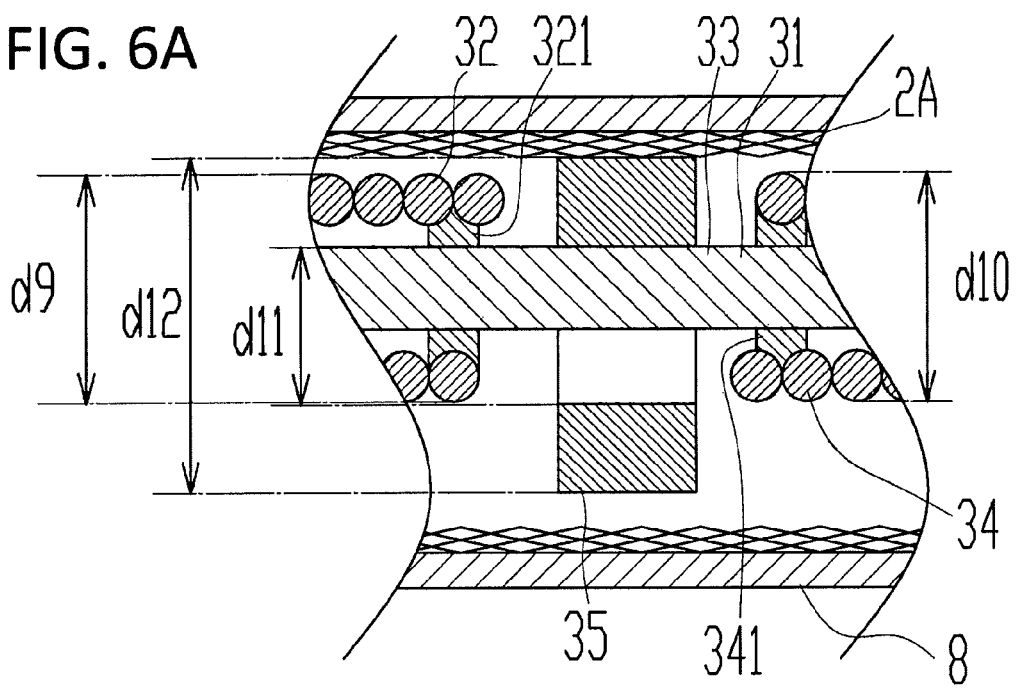
FIGS. 6A and 6B each show a partial enlarged cross-sectional view of the delivery system shown in FIGS. 5A and 5B.
Figure 6B:
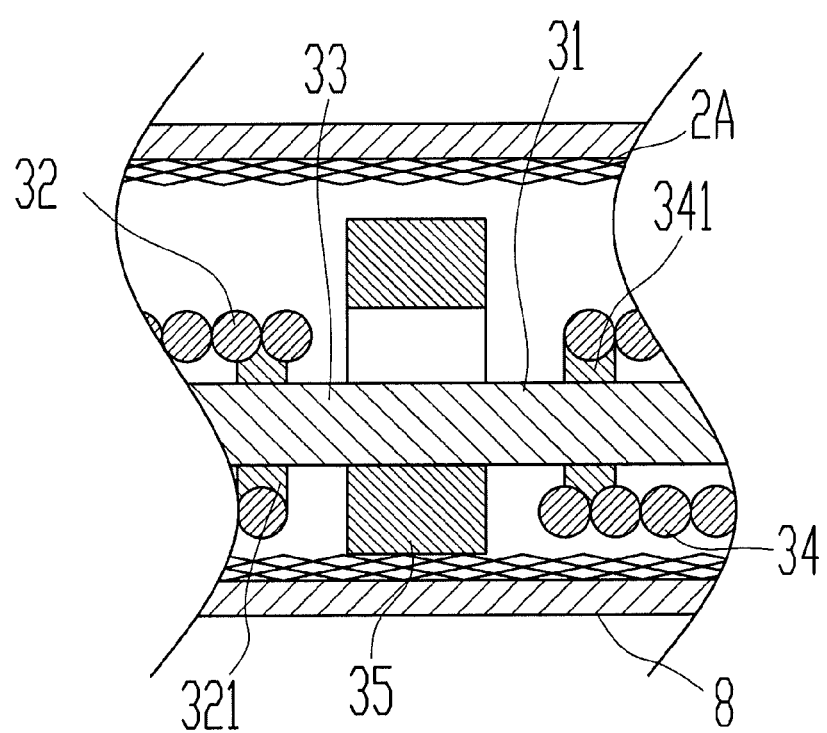

The pusher guide wire 30 further comprises a tubular member 35 that is located at a small-diameter portion 33 of the pusher guide wire 30 formed between the first coil body 32 and the second coil body 34. The small-diameter portion 33 of the pusher guide wire 30 extends through an inside of the tubular member 35. The tubular member 35 is not fixed to the core shaft 31 and is capable of moving in a radial direction relative to the core shaft 31, as shown in FIGS. 6A and 6B. Specifically, an inner diameter $d11$ of the tubular member 35 is smaller than each of an outer diameter $d9$ of the first coil body 32 and an outer diameter $d10$ of the second coil body 34 ($d9>d11$, $d10>d11$). Further, an outer diameter $d12$ of the tubular member 35 is larger than each of the outer diameter $d9$ of the first coil body 32 and the outer diameter $d10$ of the second coil body 34 ($d12>d9$, $d12>d10$).

Since the tubular member 35 is not fixed to the core shaft 31 in the configuration described above, an outer periphery of the tubular member 35 can make contact with the inner periphery of the stent 2A in an appropriate manner when the stent 2A and the pusher guide wire 30 pass through the inside of a curved blood vessel, as shown in FIGS. 6A and 6B. Further, even in a case where the core shaft 31 is rotated, the tubular member 35, the stent 2A, and the catheter 8 will not rotate. Therefore, a risk of damaging the inner wall of a blood vessel when rotating the core shaft 31 can be reduced.

Further, the stent 2A can be delivered smoothly to a target site because a clearance between the core shaft 31 and the catheter 8 can be secured by the presence of the tubular member 35.

Moreover, the core shaft 31 can rotate independently of the tubular member 35 and the catheter 8 as described above, leading to excellent operability.

Figure 5B:
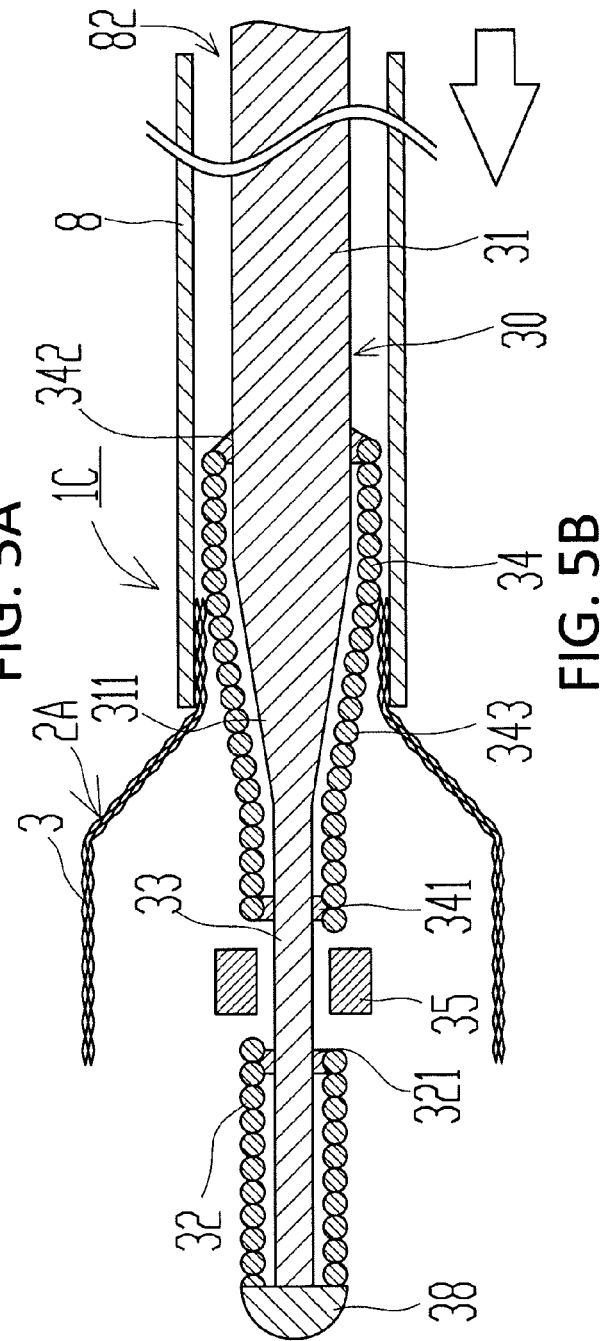

Further, a maximum outer diameter of the tapered portion 343 of the second coil body 34 is larger than the inner diameter of the stent 2A when the stent 2A is stored inside the catheter 8. Thus, the stent 2A can be pushed out of the catheter 8 in the distal direction by the tapered portion 343 of the second coil body 34, as shown in FIG. 5B. Therefore, the stent 2A can be delivered more smoothly to a target site without impairing the flexibility of the pusher guide wire 30 because a separate member does not need to be provided as a means for pressing the stent 2A.

Figure 7:
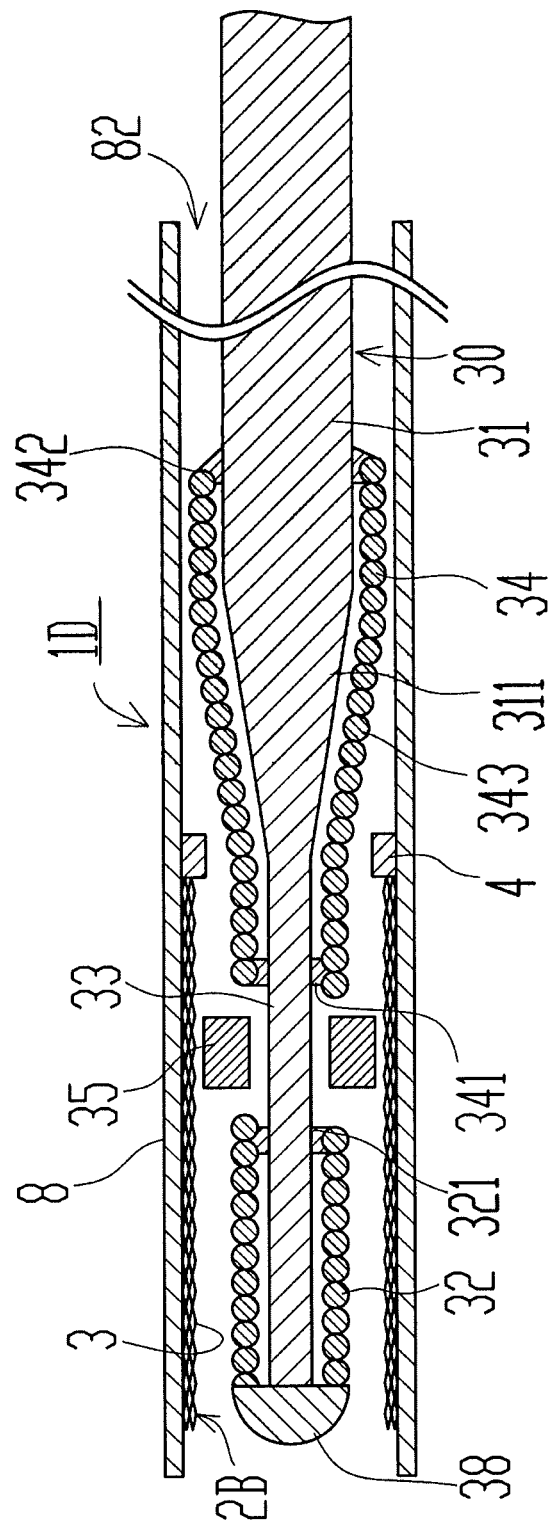
FIG. 7 shows a cross-sectional view of a delivery system according to the disclosed embodiments.

As shown in FIG. 7, a delivery system 1D comprises a self-expandable stent 2B and the pusher guide wire 30.

The stent 2B comprises the body portion 3 having a mesh-like cylindrical shape. Moreover, a proximal end engagement portion 4 is formed at a proximal end portion of the body portion 3 and protrudes toward an outer periphery of the core shaft 31. The proximal end engagement portion 4 is located between the tapered portion 343 of the second coil body 34 and the tubular member 35 in the axial direction of the core shaft 31. Note that the proximal end engagement portion 4 can be formed by joining a part of element wires of the mesh constituting the body portion 3 using, for example, a solder material. Alternatively, the proximal end engagement portion 4 can be formed by joining, for example, a radiopaque hollow tube body or coil body to an end portion of an element wire of the mesh constituting the body portion 3.

Further, an inner diameter of the stent 2B at the proximal end engagement portion 4 is designed to be smaller than the maximum outer diameter at the tapered portion 343 of the second coil body 34 when the stent 2B is stored inside the catheter 8. Therefore, the stent 2B can be pushed out of the catheter 8 in the distal direction by pressing the proximal end engagement portion 4 with the tapered portion 343 of the second coil body 34 in the distal direction. As described above, a force for directing the stent 2B in the distal direction can easily be exerted by providing the proximal end engagement portion 4 in the stent 2B. Note that the outer diameter $d12$ of the tubular member 35 is designed to be larger than the inner diameter at the proximal end engagement portion 4 of the stent 2B when the stent 2B is stored inside the catheter 8.

Below, the operating procedure of the delivery system 1D will be described.

After advancing the catheter 8 to a target site, an operator pushes the core shaft 31 of the pusher guide wire 30 in the distal direction with the intention of releasing the stent 2B stored inside the catheter 8 to the target site. Then, as shown in FIG. 8A, the tapered portion 343 of the second coil body 34 makes contact with the proximal end engagement portion 4 of the stent 2B. Then, the stent 2B is pushed out of the catheter 8 by further pushing the core shaft 31, and the stent 2B undergoes self-expansion upon release from the catheter 8.

In a case where the actual release position of the stent 2B deviates from the intended release position (the target site), the pusher guide wire 30 can be pulled in the proximal direction back inside the catheter 8, whereby a proximal end of the first coil body 32 is then brought into contact with a distal end of the tubular member 35, and a proximal end of the tubular member 35 is brought into contact with the proximal end engagement portion 4 of the stent 2B to further pull the pusher guide wire 30 back in the proximal direction, as shown in FIG. 8B. Thereby, the stent 2B can be again stored inside the catheter 8 after having been partially released from the catheter 8. The stent 2B can then be released again at an appropriate position.

Figure 9:
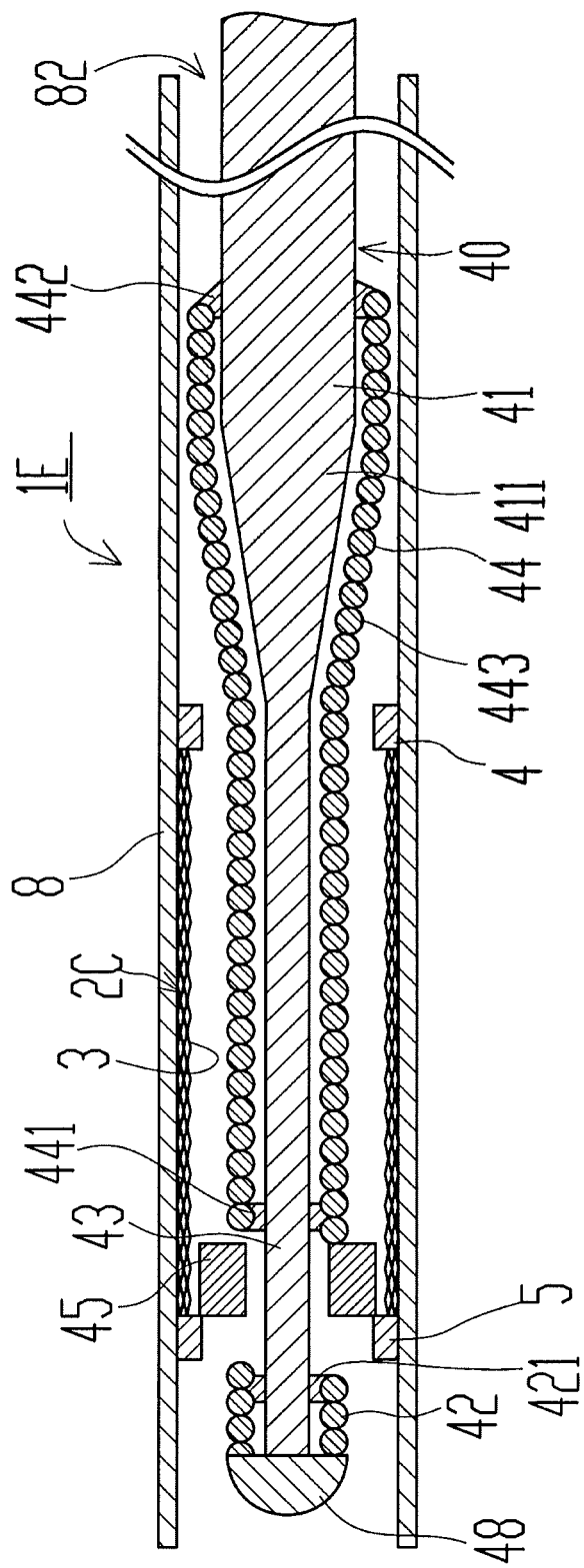
FIG. 9 shows a cross-sectional view of a delivery system according to the disclosed embodiments.

As shown in FIG. 9, a delivery system 1E comprises a self-expandable stent 2C and a pusher guide wire 40.

The stent 2C has a distal end engagement portion 5 at the distal end portion of the body portion 3. The distal end engagement portion 5 protrudes toward an outer periphery of a core shaft 41.

The pusher guide wire 40 comprises a first coil body 42 covering the core shaft 41 and fixed to the core shaft 41. A distal end portion and a proximal end portion of the first coil body 42 are joined to the core shaft 41 through a distal end portion 48 of the core shaft 41 and a first joining region 421, respectively. The pusher guide wire 40 also comprises a second coil body 44 covering the core shaft 41 and fixed to the core shaft 41 proximal to the first coil body 42 such that the first coil body 42 and the second coil body 44 are spaced apart from each other in an axial direction of the pusher guide wire 40. The second coil body 44 is joined to the core shaft 41 through second and third joining regions 441 and 442.

Further, the core shaft 41 has a tapered portion 411 with an outer diameter that increases toward a proximal end of the pusher guide wire 40, the tapered portion 411 being covered with the second coil body 44. Further, the second coil body 44 also has a tapered portion 443 with an outer diameter that increases toward the proximal end of the pusher guide wire 40.

The pusher guide wire 40 further comprises a tubular member 45 that is located at a small-diameter portion 43 of the pusher guide wire 40 formed between the first coil body 42 and the second coil body 44. The small-diameter portion 43 of the pusher guide wire 40 extends through an inside of the tubular member 45.

Here, in the case of the delivery system 1E, when the pusher guide wire 40 is pushed thereinto, a proximal end of the tubular member 45 makes contact with a distal end portion of the second coil body 44, and a distal end of the tubular member 45 makes contact with the distal end engagement portion 5 of the stent 2C. At this time, the proximal end engagement portion 4 of the stent 2C does not make contact with the pusher guide wire 40.

In the aforementioned configuration, the distal end engagement portion 5 of the stent 2C can be pushed by pushing the pusher guide wire 40 to exert a force for directing the stent 2C in the distal direction. In this case, a risk of bending the stent 2C inside the catheter 8 can be reduced, allowing the stent 2C to be delivered more smoothly.

The dimension and shape of each part described in the aforementioned embodiments may be freely selected in an appropriate manner within a range that does not depart from the spirit of the disclosed embodiments. Further, materials used shall not be limited to those described in the aforementioned embodiments.

For example, in the aforementioned delivery systems 1B to 1E, the first coil bodies 22, 32, 42 and the second coil bodies 24, 34, 44 are formed by winding one wire. Without being limited to such a construction, the first coil bodies 22, 32, 42 and the second coil bodies 24, 34, 44 may be formed by spirally twisting together two or more wires or by spirally twisting together two or more twisted wires, each twisted wire formed by twisting together two or more wires.

As described above, the rotational operability of the pusher guide wires 20, 30, 40 can be improved in a case where the first coil bodies 22, 32, 42 and the second coil bodies 24, 34, 44 are formed by twisting together two or more wires or two or more twisted wires. In particular, in a case where the tapered portion 343 of the second coil body 34 is brought into contact with the proximal end engagement portion 4 of the stent 2B to push the stent 2B in the distal direction as shown in FIG. 8A; or in a case where the proximal end of the tubular member 45 is brought into contact with the distal end portion of the second coil body 44, and the distal end of the tubular member 45 is brought into contact with the distal end engagement portion 5 of the stent 2C to push the stent 2C in the distal direction as shown in FIG. 9, the second coil bodies 34, 44 are preferably formed by spirally twisting together two or more wires or by spirally twisting together two or more twisted wires. In the pusher guide wires 30, 40 comprising the second coil bodies 34 and 44 as described above, rotational operation can be allowed while pushing in the distal direction, and thus the stents 2B and 2C can be delivered more smoothly even to the inside of a curved blood vessel.

What is claimed is:

1. A delivery system to be inserted into a catheter, the delivery system comprising:
a pusher guide wire for delivering a stent to a target site, the pusher guide wire comprising:
a core shaft;
a first coil body covering the core shaft and fixed to the core shaft;
a second coil body covering the core shaft and fixed to the core shaft at a position proximal to the first coil body, the first coil body and the second coil body being spaced apart from each other in an axial direction of the pusher guide wire; and
a tubular member disposed between the first coil body and the second coil body such that the core shaft extends through an inside of the tubular member,
wherein:
the tubular member is not fixed to the core shaft and is capable of moving in a radial direction relative to the core shaft, and
the second coil body has a tapered portion with an outer diameter that increases toward a proximal end of the pusher guide wire; and
a stent to be delivered by the pusher guide wire, the stent comprising:
a proximal end portion; and
a proximal end engagement portion that protrudes toward an outer periphery of the core shaft,
wherein when the stent is stored within the catheter:
an inner diameter of the stent at the proximal end engagement portion is smaller than a maximum outer diameter of the tapered portion,
the proximal end engagement portion is located between the tapered portion and the tubular member in an axial direction of the core shaft, and
a distal end of the stent is located distal to the tubular member.

2. The delivery system according to claim 1, wherein:
an inner diameter of the tubular member is smaller than each of an outer diameter of the first coil body and an outer diameter of the second coil body; and
an outer diameter of the tubular member is larger than each of the outer diameter of the first coil body and the outer diameter of the second coil body.

3. The delivery system according to claim 1, wherein the tubular member is formed of a radiopaque material.

4. The delivery system according to claim 2, wherein the tubular member is formed of a radiopaque material.

5. A delivery system to be inserted into a catheter, the delivery system comprising:
a pusher guide wire for delivering a stent to a target site, the pusher guide wire comprising:
a core shaft;
a first coil body covering the core shaft and fixed to the core shaft;
a second coil body covering the core shaft and fixed to the core shaft at a position proximal to the first coil body, the first coil body and the second coil body being spaced apart from each other in an axial direction of the pusher guide wire; and
a tubular member disposed between the first coil body and the second coil body such that the core shaft extends through an inside of the tubular member,
wherein the tubular member is not fixed to the core shaft and is capable of moving in a radial direction relative to the core shaft; and
a stent to be delivered by the pusher guide wire, the stent comprising:
a distal end portion; and
a distal end engagement portion that protrudes toward an outer periphery of the core shaft,
wherein when the stent is stored within the catheter:

an inner diameter of the stent at the distal end engagement portion is smaller than an outer diameter of a distal end of the tubular member, and the distal end engagement portion is located between the first coil body and the tubular member in an axial direction of the core shaft.

6. The delivery system according to claim 5, wherein:

an inner diameter of the tubular member is smaller than each of an outer diameter of the first coil body and an outer diameter of the second coil body; and an outer diameter of the tubular member is larger than each of the outer diameter of the first coil body and the outer diameter of the second coil body.

7. The delivery system according to claim 6, wherein the second coil body has a tapered portion with an outer diameter that increases toward a proximal end of the pusher guide wire.

8. The delivery system according to claim 5, wherein the second coil body has a tapered portion with an outer diameter that increases toward a proximal end of the pusher guide wire.

9. The delivery system according to claim 5, wherein the tubular member is formed of a radiopaque material.

\* \* \* \* \*